(12) United States Patent
Souda et al.

(10) Patent No.: US 7,741,511 B2
(45) Date of Patent: Jun. 22, 2010

(54) PROCESS FOR THE PREPARATION OF CARBOXYLIC ACID ESTERS

(75) Inventors: Hiroshi Souda, Toyonaka (JP); Kazunori Iwakura, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 11/837,399

(22) Filed: Aug. 10, 2007

(65) Prior Publication Data

US 2008/0009648 A1    Jan. 10, 2008

Related U.S. Application Data

(62) Division of application No. 10/994,228, filed on Nov. 23, 2004, now abandoned.

(30) Foreign Application Priority Data

Nov. 26, 2003    (JP) .............................. 2003-395147

(51) Int. Cl.
    *C07C 69/24* (2006.01)
(52) U.S. Cl. ...................... 560/124; 560/231
(58) Field of Classification Search ................. 560/124, 560/231
    See application file for complete search history.

(56) References Cited

U.S. PATENT DOCUMENTS

| | | | | |
|---|---|---|---|---|
| 4,374,760 | A |   | 2/1983 | Charles |
| 4,402,972 | A | * | 9/1983 | Martel et al. ................ 514/521 |
| 4,489,093 | A | * | 12/1984 | Martel et al. ................ 514/417 |
| 4,547,522 | A |   | 10/1985 | Martel et al. |
| 4,556,666 | A | * | 12/1985 | Tessier et al. ............... 514/351 |
| 4,607,026 | A | * | 8/1986 | Tessier et al. ................. 514/80 |
| 4,808,749 | A | * | 2/1989 | Martel et al. ................ 558/434 |
| 4,883,806 | A | * | 11/1989 | Martel et al. ................ 514/417 |
| 4,939,172 | A | * | 7/1990 | Cadiergue et al. .......... 514/531 |
| 5,019,595 | A | * | 5/1991 | Yano et al. .................. 514/531 |
| 5,093,362 | A | * | 3/1992 | Milner et al. ................ 514/531 |
| 5,262,438 | A | * | 11/1993 | Benoit et al. ................ 514/531 |
| 6,107,339 | A | * | 8/2000 | Katsuda et al. ............. 514/531 |
| 6,294,576 | B1 | * | 9/2001 | Mori .......................... 514/531 |
| 6,908,945 | B2 | * | 6/2005 | Mori .......................... 514/521 |
| 6,909,013 | B2 | * | 6/2005 | Souda et al. ................ 560/124 |
| 7,217,682 | B2 | * | 5/2007 | Mori .......................... 504/309 |
| 2005/0113581 | A1 | * | 5/2005 | Souda et al. ................ 546/315 |
| 2008/0009648 | A1 | * | 1/2008 | Souda et al. ................ 560/124 |
| 2008/0033194 | A1 | * | 2/2008 | Souda et al. ................. 556/56 |

FOREIGN PATENT DOCUMENTS

| | | |
|---|---|---|
| EP | 0 779 269 A1 | 6/1997 |
| EP | 1227077 A2 | 7/2002 |
| JP | 60-64945 A | 4/1985 |
| JP | 2-13649 B2 | 4/1990 |
| JP | 6340870 A * | 12/1994 |
| JP | 9-188649 A | 7/1997 |
| JP | 11-228491 A | 8/1999 |
| JP | 2002-293759 A | 10/2002 |
| JP | 2003-292471 A | 10/2003 |
| JP | 2004-83531 A | 3/2004 |

OTHER PUBLICATIONS

English language abstract of JP 06 340870 A (Dec. 13, 1994).
Shah et al., Indian J. Chem., vol. 23A, pp. 632-635, (1993).
Goel, S. C., Synthesis and Reactivity in Inorganic and Metal-organic Chemistry, vol. 15, No. 4, pp. 533-544, (1985).
Mehrotra et al., Indian J. Chem., vol. 11, No. 8, pp. 814-816, (1973).
A. Shah, A. Sing and R. C. Mehrotra, Synthesis and characterization of alkoxo- and chloro-aryloxo derivatives of titanium and zirconium, Indian Journal of Chemistry, vol. 32 A, Jul. 1993, pp. 632-635.
Mehrotra, Ram Charan, Mixed tertiary alkoxides of zirconium, J. Indian Chem. Soc., (1954), 31, 904-910 (Abstract).

* cited by examiner

*Primary Examiner*—Elvis O Price
(74) *Attorney, Agent, or Firm*—Birch, Stewart, Kolasch & Birch, LLP

(57) ABSTRACT

There is provided a process for preparing a carboxylic acid ester of formula (3):

$$R^2COOR^1 \qquad (3)$$

wherein $R^1$ is
an alkyl group which may be substituted,
an alkenyl group which may be substituted,
an alkynyl group which may be substituted,
an aralkyl group which may be substituted, or
a heteroarylalkyl group which may be substituted, and $R^2$ is
an alkyl group which may be substituted,
an alkenyl group which may be substituted,
an alkynyl group which may be substituted,
an aryl group which may be substituted,
a heteroaryl which may be substituted,
an aralkyl group which may be substituted, or
a heteroarylalkyl group which may be substituted,
which process is characterized by the steps of reacting a monohydroxy compound of formula (1):

$$R^1OH \qquad (1)$$

wherein $R^1$ is as defined above, with a zirconium compound of formula (6):

$$Zr(OR^8)_4 \qquad (6)$$

wherein $R^8$ is an alkyl group or an aryl group which may be substituted and is not the same as $R^1$, to prepare a zirconium catalyst, and reacting a carboxylic acid of formula (2):

$$R^2COOH \qquad (2)$$

wherein $R^2$ is as defined above, with the monohydroxy compound of formula (1) in the presence of the zirconium catalyst.

14 Claims, No Drawings

PROCESS FOR THE PREPARATION OF CARBOXYLIC ACID ESTERS

This application is a Divisional of application Ser. No. 10/994,228, filed on Nov. 23, 2004 now abandoned, the entire contents of which are hereby incorporated by reference and for which priority is claimed under 35 U.S.C. §120.

BACKGROUND OF THE INVENTION

Field of the Invention

The present invention relates to a process for the preparation of carboxylic acid esters, in particular of a cyclopropanecarboxylic acid with an alcohol.

There have been known esterification reactions of a carboxylic acid with a hydroxyl compound thorough dehydration using an acid catalyst such as sulfuric acid, or p-toluenesulfonic acid (e.g., JP-A No. H09-188649 and JP-A No. H11-228491.), or using dicyclohexylcarbodiimide or diisopropylcarbodiimide (e.g., JP-A No. S60-64945).

It is also known that such reaction can be conducted by using certain zirconium compound as a catalyst (JP-A No. 2002-293759).

SUMMARY OF THE INVENTION

According to the present invention, an esterification-reaction by condensing a monohydroxy compound with a carboxylic acid can be carried out in good selectivity.

The present invention provides
a process for preparing a carboxylic acid ester of formula (3):

$$R^2COOR^1 \quad (3)$$

wherein $R^1$ is
an alkyl group which may be substituted,
an alkenyl group which may be substituted,
an alkynyl group which may be substituted,
an aralkyl group which may, be substituted, or
a heteroarylalkyl group which may be substituted, and $R^2$ is
an alkyl group which may be substituted,
an alkenyl group which may be substituted,
an alkynyl group which may be substituted,
an aryl group which may be substituted,
a heteroaryl which may be substituted,
an aralkyl group which may be substituted, or
a heteroarylalkyl group which may be substituted,
which process comprises the steps of reacting a monohydroxy compound of formula (1):

$$R^1OH \quad (1)$$

wherein $R^1$ is as defined above, with a zirconium compound of formula (6):

$$Zr(OR^8)_4 \quad (6)$$

wherein $R^8$ is an alkyl group or an aryl group which may be substituted and is not the same as $R^1$, to prepare a zirconium catalyst, and
reacting a carboxylic acid of formula (2):

$$R^2COOH \quad (2)$$

wherein $R^2$ is as defined above, with the monohydroxy compound of formula (1) in the presence of the zirconium catalyst.

Next, the step of preparing the zirconium catalyst by reacting a zirconium compound with the monohydroxy compound of formula (1) (hereinafter, referred to as monohydroxy compound (1).) is described.

The zirconium compound of formula (6) (hereinafter, referred to as zirconium compound (6)):

$$Zr(OR^8)_4 \quad (6)$$

wherein $R^8$ is an alkyl group or an aryl group which may be substituted and $R^8$ is not the same as $R^1$, is described.

Examples of the alkyl group represented by $R^8$ include, for example,
a $C_{1-6}$ straight or branched chain or cyclic alkyl group such as methyl, ethyl, propyl, isopropyl, cyclopropyl, butyl, sec-butyl, tert-butyl, pentyl, hexyl, cyclohexyl.

Examples of the aryl group include, for example, phenyl, and naphthyl(1-naphthyl, and 2-naphthyl), and preferred is a phenyl group.

The aryl group may be substituted with an alkyl group such as a C1-4 alkyl group (e.g., methyl, ethyl, n-propyl, i-propyl) or butyl(e.g. t-butyl)).

Preferred $R^8$ is $C_{1-4}$ alkyl.

Typical examples of the zirconium compound (6) include, for example, tetramethoxyzirconium, tetraethoxyzirconium, tetrapropoxyzirconium, tetraisopropoxyzirconium, tetrabutoxyzirconium, tetra(tert-butoxy)zirconium, tetraphenoxy zirconium or mixture of two or more of them. In view of ready-availability, any one tetraalkoxyzirconium selected from the group consisting of tetramethoxyzirconium, tetraethoxyzirconium, tetrapropoxyzirconium and tetrabutoxyzirconium is preferably used.

The zirconium compound (6) may be used in a powder or solid form, or may be used in a form of solution just as it is available. Also, it may be used as a complex with a compound having a coordination property such as tetrahydrofuran or tetramethylethylenediamine.

Examples of the alkyl group, which may be substituted, represented by $R^1$, in the monohydroxy compound (1) include, for example, a $C_{1-10}$ straight, branched or cyclic alkyl group such as methyl, ethyl, propyl, isopropyl, cyclopropyl, butyl, cyclopropylmethyl, sec-butyl, tert-butyl, pentyl, hexyl, cyclohexyl, heptyl, octyl, nonyl, decyl or menthyl, and
a $C_{1-10}$ straight, branched or cyclic alkyl group substituted with halogen (e.g., fluorine, chlorine, bromine and iodine).

Specific examples of the monohydroxy compound (1), wherein $R^1$ is an alkyl which may be substituted, referred to as the alkyl alcohol, include, for example, methyl alcohol, ethyl, alcohol, propyl alcohol, isopropyl alcohol, butyl alcohol, sec-butyl alcohol, tert-butyl alcohol, pentyl alcohol, neopentyl alcohol; amyl alcohol, hexyl alcohol, octyl alcohol, decyl alcohol, fluoroethyl alcohol, difluoroethyl alcohol, trifluoroethyl alcohol, tetrafluoroethyl alcohol, pentafluoroethyl alcohol, 3,3-dibromo-2-propen-1-ol, perfluoropropyl alcohol, hexafluoroisopropyl alcohol, perfluorobutyl alcohol, perfluoropentyl alcohol, perfluorohexyl alcohol, perfluorooctyl alcohol, and perfluorodecyl alcohol.

Examples of the alkenyl group which may be substituted, represented by $R^1$, include, for example, a $C_{3-10}$ straight, branched or cyclic alkenyl group which may be substituted with a group selected from the group consisting of a C1-4 alkyl group, a $C_{2-4}$ alkenyl group, a $C_{2-4}$ alkynyl group and an oxo group. Specific examples thereof include, for example, hydroxycyclopentenone compound such as 4-hydroxy-3-methyl-2-(2-propenyl)-2-cyclopenten-1-one, or 4-hydroxy-3-methyl-2-(2-propynyl)-2-cyclopenten-1-one.

Examples of the alkynyl group which may be substituted, represented by $R^1$, include, for example, a straight, branched or cyclic $C_{3-10}$ alkynyl group which may be substituted with a halogen and may contain a double bond such as 4-methyl-hept-4-ene-1-yne-3-ol or 4-fluorohept-4-ene-1-yne-3-ol.

Examples of the aralkyl group which may be substituted, represented by $R^1$, include, for example, a $C_{7-20}$ aralkyl group such as benzyl, phenylethyl, phenylpropyl, naphthylmethyl, naphthylethyl, or anthracenylmethyl, and a $C_{7-20}$ aralkyl group substituted with at least one member selected from the group consisting of a halogen atom, and $C_{1-14}$ alkyl, phenyl, phenoxy, $C_{1-4}$ alkoxy and $C_{2-4}$ alkoxyalkyl groups which may be substituted with a halogen atom, a propargyl group, a cyano group, a nitro group and a $C_3$ haloacyloxy-methyl group (e.g., trifluoroacetyloxy-methyl).

Preferably, $R^1$ is a benzyl which may be substituted, and more preferably $R^1$ is a benzyl group which may be substituted with at least one member selected from the group consisting of a halogen atom, a methyl group, a phenyl group, a phenoxy group, a halo-phenoxy group, a propargyl group, a halomethyl, a halomethoxy group, a cyano group, a nitro group, a methoxymethyl group and a halogen-substituted methoxymethyl group.

Furthermore preferably, $R^1$ is a benzyl group which may be substituted with at least one member selected from the group consisting of a halogen atom, a methyl group, a halomethyl, a halomethoxy group: a methoxymethyl group and a halogen-substituted methoxymethyl.

Yet furthermore preferably, $R^1$ is benzyl group substituted with a halogen atom.

Specific examples of the aralkyl alcohol having the aralkyl group which may be substituted, represented by $R^1$, include, for example, benzyl alcohol, 2-methyl-3-phenylbenzyl alcohol, 2,3,5,6-tetrafluorobenzyl alcohol, 2,3,5,6-tetrafluoro-4-methylbenzyl alcohol, 2,3,5,6-tetrafluoro-4-methoxybenzyl alcohol, 2,3,5,6-tetrafluoro-4-(methoxymethyl)benzyl alcohol, 2,3,5,6-tetrafluoro-4-propargylbenzyl alcohol, 2,3,5,6-tetrafluoro-4-(difluoromethyl)benzyl alcohol, 2,3,5,6-tetrafluoro-4-(difluoromethoxy)benzyl alcohol, 2,3,5,6-tetrafluoro-4-(2,2,2-trifluoroacetyloxy)methylbenzyl alcohol, 4-(trifluoromethyl)benzyl alcohol, 2,3,4,5-tetrafluoro-6-methylbenzyl alcohol, 3-phenylbenzyl alcohol, 2,6-dichlorobenzyl alcohol, 3-phenoxybenzyl alcohol, 2-hydroxy-2-(3-phenoxyphenyl)ethanenitrile, 2-hydroxy-2-{4-(methoxymethyl)phenyl}ethanenitrile, 2-{3-(4-chlorophenoxy)phenyl}-2-hydroxyethanenitrile, 2-(4-amino-2,3,5,6-tetrafluorophenyl)-2-hydroxyethanenitrile, 2-(4-fluoro-3-phenoxyphenyl)-2-hydroxyethanenitrile, (2-methylphenyl)methyl alcohol, (3-methylphenyl)methyl alcohol, (4-methylphenyl)methyl alcohol, (2,3-dimethylphenyl)methyl alcohol, (2,4-dimethylphenyl)methyl alcohol, (2,5-dimethylphenyl)methyl alcohol, (2,6-dimethylphenyl)methyl alcohol, (3,4-dimethylphenyl)methyl alcohol, (2,3,4-trimethylphenyl)methyl alcohol, (2,3,5-trimethylphenyl)methyl alcohol, (2,3,6-trimethylphenyl)methyl alcohol, (3,4,5-trimethylphenyl)methyl alcohol, (2,4,6-trimethylphenyl)methyl alcohol, (2,3,4,5-tetramethylphenyl)methyl alcohol, (2-3,4,6-tetramethylphenyl)methyl alcohol, (2,3,5,6-tetramethylphenyl)methyl alcohol, (pentamethylphenyl)methyl alcohol, (ethylphenyl)methyl alcohol, (propylphenyl)methyl alcohol, (isopropylphenyl)methyl alcohol, (butylphenyl)methyl alcohol, (sec-butylphenyl)methyl alcohol, (tert-butylphenyl)methyl alcohol, (pentylphenyl)methyl alcohol, (neopentylphenyl)methyl alcohol, (hexylphenyl)methyl alcohol, (octylphenyl)methyl alcohol, (decylphenyl)methyl alcohol, (dodecylphenyl)methyl alcohol, (tetradecylphenyl) methyl alcohol, naphthylmethyl alcohol, anthracenylmethyl alcohol, 1-phenylethyl alcohol, 1-(1-naphthyl)ethyl alcohol, 1-(2-naphthyl)ethyl alcohol, 4-(prop-2-ynyl)phenylmethane-1-ol, 3-(prop-2-ynyl)phenylmethane-1-ol, 4-prop-2-enylindan-1-ol, 4-phenylindan-2-ol, and alkoxyaralkyl alcohol obtained by replacing the halogen atom of the aforementioned halo-aralkyl alcohol to methoxy, ethoxy, propoxy, isopropoxy, butoxy, sec-butoxy, tert-butoxy and the like, cyanoaralkyl alcohol and nitroaralkyl alcohol.

Examples of the heteroarylalkyl alcohol having the heteroarylalkyl group which may be substituted represented by $R^1$ include, for example, 4-(2-thienyl)indan-2-ol, (2,3,6-trifluoro-4-pyridyl)methane-1-ol, (1-prop-2-ynyl-2-methylindole-3-yl)methane-1-ol, {1-prop-2-ynyl-2-(trifluoromethyl)indole-3-yl}methane-1-ol, 2-furylmethyl alcohol, 3-furylmethyl alcohol, (5-phenoxy-3-furyl)methyl alcohol, (5-benzyl-3-furyl)methane-1-ol, {5-(difluoromethyl)-3-furyl}methane-1-ol, 5-propargylfurfuryl alcohol, (5-methylisoxazol-3-yl)methane-1-ol, 1-{2-(trifluoromethyl)-1,3-thiazol-4-yl}prop-2-yne-1-ol, 1-{2-(trifluoromethoxy)-1,3-thiazol-4-yl}prop-2-yne-1-ol, 1-{1-prop-2-ynyl-5-(trifluoromethyl)pyrrole-3-yl}prop-2-yne-1-ol, (1-prop-2-ynylpyrrole-3-yl)methane-1-ol, 3-(hydroxymethyl)-1-propynyl-imidazolidin-2,4-dione, 2-(hydroxymethyl)-4,5,6,7-tetrahydroisoindole-1,3-dione, {1-(2-propynyl)pyrrole-3-yl}methane-1-ol, 5-(hydroxymethyl)-4-methyl-(2-propynyl)-1,3-thazolin-2-one, {1-(2-propynyl)-5-(trifluoromethyl)-4-pyrazolyl}methane-1-ol, 1-{1-(2-propynyl)-5-(trifluoromethyl)pyrrole-3-yl}prop-2-yne-1-ol, 1-{2-(trifluoromethyl)-1,3-thiazol-4-yl}prop-2-yne-1-ol, and 1-{2-(trifluoromethoxy)-1,3-thiazol-4-yl}prop-2-yne-1-ol.

Among the monohydroxy compound (1), preferred is a primary alcohol.

The zirconium catalyst thus prepared includes, for example, a zirconium compound of formula (8) (hereinafter, referred to as zirconium compound (8)):

$$Zr(OR^1)_n(OR^8)_{4-n} \quad (8)$$

wherein $R^1$ is as defined in connection with formula (1), and $R^8$ is as defined in connection with formula (6), and n is an integer of 1 to 4, or mixtures thereof, which is obtained by reacting the zirconium compound (6) with the monohydroxy compound (1). The reaction is usually accompanied by by-production of a monohydroxy compound of formula (7):

$$R^8OH \quad (7)$$

wherein $R^8$ is as defined, hereinafter, referred to as monohydroxy compound (7).

The more amount of the monohydroxy compound (1) is employed, the larger n in the zirconium compound (8) is thus the monohydroxy compound (7) is produced more. Zirconium compounds (8) having different n may also be included in the reaction system.

A preferred zirconium compound is a zirconium compound (8) wherein $R^1$ is an aralkyl group which may be substituted and $R^8$ is an alkyl group which may be substituted or an aryl group which may be substituted, and n is an integer of 1 to 4, and a zirconium compound (8) wherein $R^1$ represents a heteroarylalkyl group which may be substituted such as (1-prop-2-ynyl-2-methylindole-3-yl)methane-1-yl, {1-prop-2-ynyl-2-(trifluoromethyl)indole-3-yl}methane-1-yl, 4-(2-thienyl)indan-2-yl, (2,3,6-trifluoro-4-pyridyl)methane-1-yl, 2-furylmethyl, 3-furylmethyl, (5-phenoxy-3-furyl)methyl, (5-benzyl-3-furyl)methyl, {5-(difluoromethyl)-3- furyl}methyl, 5-propargylfurfuryl, (5-methylisoxazol-3-yl)methyl, 1-{2-(trifluoromethyl)-1,3-thiazol-4-yl}prop-2-yne-1-yl, 1-{2-(trifluoromethoxy)-1,3-thiazol-4-yl}prop-2-yne-1-yl, 1-{1-prop-2-ynyl-5-(trifluoromethyl)pyrrole-3-yl}prop-2-yne-1-yl, (1-prop-2-ynylpyrrole-3-yl)methyl, 1-propynyl-imidazolidin-2,4-dione-3-methyl, 3-methyl-2-(2-propenyl)-2-cyclopenten-1-one-4-yl, 3-methyl-2-(2-propynyl)-2-cyclopenten-1-one-4-yl, 4,5,6,7-tetrahydroisoindole-1,3-dione-2-methyl, {1-(2-propynyl)pyrrole-3-yl}methyl, or 4-methyl-(2-propynyl)-1,3-thazolin-2-one-5-methyl, and $R^8$ is an alkyl group which may be substituted or an aryl group which may be substituted, and n is an integer of 1 to 4.

In the preferred embodiments above, more preferably, $R^8$ is a $C_{1-4}$ alkyl group, and $R^1$ is a benzyl alcohol which may be substituted, and still more preferably $R^1$ is a benzyl group which may be substituted with at least one member selected from the group consisting of a halogen atom, a propargyl, group, and methyl, methoxy, phenyl, phenoxy and methoxymethyl groups which may be substituted, a cyano group and nitro.

Furthermore preferably, $R^1$ is a benzyl group which may be substituted with at least one member selected from the group consisting of a halogen atom, and methyl, methoxy, and methoxymethyl groups which may be substituted with halogen.

Yet furthermore preferably, $R^1$ is benzyl alcohol substituted with a halogen atom.

The by-produced monohydroxy compound (7) is preferably removed from the reaction system by distillation or the like as it is produced. A solution of the zirconium compound (6) in the monohydroxy compound (7) may be available and is used as such solution, but the monohydroxy compound (7) may also be removed from a reaction system by a suitable operation including the above-mentioned operation to reduce a side-reaction in the esterification reaction step.

The above operation may be carried out with or without solvent, and has no limitation in the amount of the solvent: when used.

Preferably used is a solvent having higher boiling point than that of the monohydroxy compound (7), or a solvent that forms an azeotropic mixture with the monohydroxy compound (7) or water produced by the esterification reaction, or a mixture of the solvents. Examples of the solvent include, for example, a halogenated hydrocarbon solvent such as dichloromethane, chloroform and 1,2-dichloroethane; aliphatic hydrocarbon solvent such as hexane, heptane, octane and nonane; aromatic hydrocarbon solvent such as benzene, toluene, xylene and chlorobenzene; and ether solvent such as tert-butyl methyl ether, dibutyl ether, dioxane and tetrahydrofuran.

The reaction is usually conducted under an atmosphere of inert gas such as argon and nitrogen, and may be conducted under a normal, pressurized or reduced pressure, preferably under normal or reduced pressure.

The reaction is usually conducted in a temperature range of approximately from 20 to 200° C. Preferably, the reaction is conducted at such a temperature that the monohydroxy compound (7) can be removed by distillation or distilled as an azeotropic mixture with a suitable solvent.

The monohydroxy compound (1) is preferably used in the amount of not less than 5 moles per mol of the zirconium compound (6), thereby a zirconium, compound (7) wherein n=4 is obtained as a major component. Alternatively, the monohydroxy compound (1) may be used in an excess amount as a solvent.

In the above operation, the reaction of a zirconium compound (6) with a monohydroxy compound (1) and the removal of a hydroxy compound (7) produced may, for example, be conducted concurrently or sequentially. Here, "sequentially" means the case that after reacting the zirconium compound (6) with the monohydroxy compound (1), the removal of the hydroxy compound (7) is conducted. In the case of using a zirconium compound (6) as solution, the hydroxy compound (7) usually used as solvent thereof may firstly removed, and then the resultant zirconium compound (6) may be reacted with the monohydroxy compound (1).

Of course, the removal of the hydroxy compound (7) in that case may be conducted concurrently or sequentially.

Specific examples of the zirconium compound (8) include, for example, benzyloxy-trimethoxyzirconium, 2,3,5,6-tetrafluoro-4-methylbenzyloxy-trimethoxyzirconium, 2,3,5,6-tetrafluoro-4-(methoxymethyl)-benzyloxy-trimethoxyzirconium, benzyloxy-triethoxyzirconium, 2,3,5,6-tetrafluoro-4-methylbenzyloxy-triethoxyzirconium, 2,3,5,6-tetrafluoro-4-(methoxymethyl)benzyloxy-triethoxy zirconium, benzyloxy-tripropoxyzirconium, 2,3,5,6-tetrafluoro-4-methylbenzyloxy-tripropoxyzirconium, 2,3,5,6-tetrafluoro-4-(methoxymethyl)benzyloxy-tripropoxyzirconium, benzyloxy-triisopropoxyzirconium, 2,3,5,6-tetrafluoro-4-methylbenzyloxy-triisopropoxyzirconium, 2,3,5,6-tetrafluoro-4-(methoxymethyl)benzyloxy-triisopropoxyzirconium, benzyloxy-tributoxyzirconium, 2,3,5,6-tetrafluoro-4-methylbenzyloxy-tributoxyzirconium, 2,3,5,6-tetrafluoro-4-(methoxymethyl)benzyloxy-tributoxyzirconium, benzyloxy-tri(tert-butoxy)zirconium, 2,3,5,6-tetrafluoro-4-methylbenzyloxy-tri(tert-butoxy)zirconium, 2,3,5,6-tetrafluoro-4-(methoxymethyl)benzyloxy-tri(tert-butoxy)zirconium, dibenzyloxy-dimethoxyzirconium, di(2,3,5,6-tetrafluoro-4-methylbenzyloxy)dimethoxyzirconium, di{2,3,5,6-tetrafluoro-4-(methoxymethyl) benzyloxy}dimethoxyzirconium, dibenzyloxy-diethoxyzirconium, di(2,3,5,6-tetrafluoro-4-methylbenzyloxy)diethoxyzirconium, di{2,3,5,6-tetrafluoro-4-(methoxymethyl) benzyloxy}diethoxyzirconium, dibenzyloxy-dipropoxyzirconium, di(2,3,5,6-tetrafluoro-4-methylbenzyloxy)dipropoxyzircorium, di{2,3,5,6-tetrafuoro-4-(methoxyethyl) benzyloxy}dipropoxyzirconium, dibenzyloxy-diisopropoxyzirconium, di(2,3,5,6-tetrafluoro-4-methylbenzyloxy)diisopropoxyzirconium, di{2,3,5,6-tetrafluoro-4-(methoxymethyl) benzyloxy}diisopropoxyzirconium, dibenzyloxy-dibutoxyzirconium, di(2,3,5,6-tetrafluoro-4-methylbenzyloxy)dibutoxyzirconium, di{2,3,5,6-tetrafluoro-4-(methoxymethyl)benzyloxy}dibutoxyzirconium, dibenzyloxy-di(tert-butoxy)zirconium, di(2,3,5,6-tetrafluoro-4-methylbenzyloxy)di(tert-butoxy)-zirconium, di{2,3,5,6-tetrafluoro-4-(methoxymethyl)benzyloxy}di(tert-butoxy)zirconium, tribenzyloxy-methoxyzirconium, tri(2,3,5,6-tetrafluoro-4-methylbenzyloxy)methoxyzirconium, tri{2,3,5,6-tetrafluoro-4-(methoxymethyl)benzyloxy}methoxy-zirconium, tribenzyloxy-ethoxyzirconium, tri(2,3,5,6-tetrafluoro-4-methylbenzyloxy)ethoxyzirconium, tri{2,3,5,6-tetrafluoro-4-(methoxymethyl)benzyloxy}ethoxy-zirconium, tribenzyloxy-propoxyzirconium, tri(2,3,5,6-tetrafluoro-4-methylbenzyloxy)propoxyzirconium, tri{2,3,5,6-tetrafluoro-4-(methoxymethyl)benzyloxy}propoxy-zirconium, tribenzyloxy-isopropoxyzirconium, tri(2,3,5,6-tetrafluoro-4-methylbenzyloxy)isopropoxy zirconium, tri{2, 3,5,6-tetrafluoro-4-(methoxymethyl) benzyloxy}isopropoxyzirconium, tribenzyloxybutoxyzirconium, tri(2,3,5,6-tetrafluoro-4-methylbenzyloxy)butoxyzirconium, tri{2,3,5,6-tetrafluoro-4-(methoxymethyl)benzyloxy}butoxy-zirconium, tribenzyloxy(tert-butoxy)zirconium, tri(2,3,5,6-tetrafluoro-4-methylbenzyloxy)(tert-butoxy)-zirconium, tri{2,3,5,6-tetrafluoro-4-(methoxymethyl)benzyloxy}(tert-butoxy)zirconium, tetra(benzyloxy)zirconium, tetra(2,3,5,6-tetrafluoro-4-methylbenzyloxy)zirconium, and tetra{2,3,5,6-tetrafluoro-4-(methoxymethyl)benzyloxy}zirconium. Preferred are the zirconium compounds (8) wherein n=4 such as tetra(benzyloxy)zirconium, tetra(2,3,5,6-tetrafluoro-4-methylbenzyloxy)zirconium, and tetra{2,3,5,6-tetrafluoro-4-(methoxymethyl)benzyloxy}zirconium.

The zirconium catalyst prepared by the present step may be isolated from the reaction system, and then used in the subsequent esterification reaction step, or may be used as a solution or slurry obtained. The esterification catalyst may be prepared for every batch of the esterification reaction step, or may be prepared for a plurality of batches at one time and used in the esterification reaction step in a suitable amount.

Next, the step of reacting the monohydroxy compound (1) with the carboxylic acid of formula (2) (hereinafter, referred to as carboxylic acid (2)) in the presence of the zirconium catalyst to obtain the carboxylic acid ester of formula (3) (hereinafter, referred to as carboxylic acid ester (3)) is described.

Examples of the alkyl group represented by $R^2$ include, for example, a straight, branched or cyclic $C_{1-20}$ alkyl group such as methyl, ethyl, propyl, isopropyl, cyclopropyl, butyl, sec-butyl, tert-butyl, pentyl, hexyl, cyclohexyl, menthyl, heptyl, octyl, nonyl, decyl, undecyl, dodecyl, tridecyl, tetradecyl, pentadecyl, hexadecyl, heptadecyl, octadecyl, nonadecyl, and icosanyl.

Examples of the alkenyl group represented by $R^2$ include, for example, a straight, branched or cyclic $C_{2-10}$ alkenyl group such as vinyl, 1-methylvinyl, 1-propenyl, 2-methyl-1-propenyl, 1-butenyl, 3-methyl-2-butenyl, hexenyl, heptenyl, octenyl nonenyl or decenyl.

Examples of the alkynyl group represented by $R^2$ include, for example, a straight or branched $C_{2-10}$ alkynyl group such as propargyl, butynyl, pentynyl, hexynyl, heptynyl, octynyl, nonynyl or decynyl.

Examples of the aralkyl group represented by $R^2$ include, for example, a $C_{7-20}$ aralkyl group such as benzyl, naphthylmethyl, or anthracenylmethyl.

Examples of the aryl group represented by $R^2$ include, for example, a $C_{6-20}$ aryl group such as phenyl, 1-naphthyl or 2-naphthyl.

Examples of the heteroaryl group represented by $R^2$ include, for example, pyridyl, thienyl and qunilyl groups.

Examples of the heteroarylalkyl group represented by $R^2$ include, for example, a furanylmethyl, pyridylmethyl, imidazolylmethyl, pyrazolylmethyl, oxazolylmethyl, thizolylmethyl, isoxazolylmethyl, thienylmethyl, indolylmethyl, pyrrolylmethyl and quinolylmethyl.

The alkyl, alkenyl and alkynyl groups, represented by $R^2$ may be substituted with a member selected from Group A consisting of a halogen, a carboxyl group, an aryl, alkoxy, alkoxyalkyl, and alkoxycarbonyl groups which may be substituted with a halogen atom, alkoxyimino, alkylsulfonyl, alkylsulfonyloxy and alkylsulfinyl.

The aralkyl, aryl and heteroarylalkyl groups, represented by $R^2$ may be substituted with a member selected from Group B consisting of a halogen, a carboxyl group, and alkyl, alkenyl, alkynyl, aryl aralkyl, alkoxy, alkoxyalkyl and alkoxycarbonyl groups which may be substituted with a halogen atom, and alkylenedioxy(e.g., methylenedioxy).

Examples of the halogen atom in Group A and B include, for example, fluorine, chlorine, bromine and iodine.

Examples of the alkoxy group in Group A and B include, for example, a $C_{1-10}$ alkoxy group such as methoxy, ethoxy, propoxy, isopropoxy, butoxy, sec-butoxy or tert-butoxy;

Examples of the alkoxycarbonyl group which may be substituted with halogen in Group A and B include, for example, a $C_{2-10}$ alkoxycarbonyl group such as methoxycarbonyl, ethoxycarbonyl, propoxycarbonyl, isopropoxycarbonyl, butoxycarbonyl, sec-butoxycarbonyl or tert-butoxycarbonyl, and a halo-substituted $C_{3-10}$ alkoxycarbonyl group such as 2,2,2-trifluoro-1-(trifluoromethyl)ethoxycarbonyl, and preferred is a $C_{3-5}$ alkoxycarbonyl group which may be substituted with halogen.

Examples of the alkoxyimino group in Group A include, for example, a $C_{1-10}$ alkoxyimino group such as methoxyimino, ethoxyimino or propoxyimino, and preferred is $C_{1-3}$ alkoxyimino group.

Examples of the alkylsulfonyl group in Group A include, for example, a $C_{1-10}$ alkylsulfonyl group such as methylsulfonyl, ethylsulfonyl, propylsulfonyl, isopropylsulfonyl or tert-butylsulfonyl, and preferred is a $C_{1-4}$ alkylsulfonyl group.

Examples of the alkylsulfonyloxy group in Group A include, for example, a $C_{1-10}$ alkylsulfonyloxy group such as methylsulfonyloxy, ethylsulfonyloxy, propylsulfonyloxy, isopropylsulfonyloxy or tert-butylsulfonyloxy, and preferred is a $C_{1-4}$ alkylsulfonyloxy group.

Examples of the alkyl group in Group B include, for example, a $C_{1-20}$ alkyl group as defined above, and typical examples thereof include, for example, methyl, ethyl, propyl, isopropyl, cyclopropyl, butyl, sec-butyl, tert-butyl, pentyl, hexyl, cyclohexyl and menthyl, and preferred is a $C_{1-6}$ alkyl.

Examples of the alkenyl group in Group B include, for example, $C_{2-10}$ alkenyl group as defined above and typical examples thereof include, for example, vinyl, 1-methylvinyl, 1-propenyl, 2-methyl-1-propenyl, 1-butenyl and 3-methyl-2-butenyl, and preferred is a $C_{2-5}$ alkenyl.

Examples of the alkynyl group in Group B include $C_{2-10}$ alkynyl, group as defined above, and typical examples thereof include, for example, propargyl.

Examples of the aryl group in Group A and B include, for example, a $C_{6-20}$ aryl group as defined above, and typical examples thereof such as phenyl, 1-naphthyl or 2-naphthyl.

Examples of the alkenyl group which may be substituted with halogen, represented by $R^2$, include, for example, 2,2-dichlorovinyl, 2,2-dibromovinyl, 2-chloro-2-fluorovinyl, 2-chloro-2-trifluoromethylvinyl, 2-bromo-2-tribromomethylvinyl, and the like.

Examples of the carboxylic acid (2) include, for example, acetic acid, propionic acid, butyric acid, isobutyric acid, valeric acid, isovaleric acid, pivalic acid, hexanoic acid, heptanoic acid, octanoic acid, nonanoic acid, decanoic acid, lauric acid, myristic acid, palmitic acid, stearic acid, acrylic acid, propiolic acid, methacrylic acid, crotonic acid, isocrotonic acid, fumaric acid, maleic acid, mesaconic acid, citraconic acid, cinnamic acid, benzoic acid, naphthoic acid, toluic acid, anisic acid, piperonylic acid, nicotinic acid, isonicotinic acid, phenylacetic acid, 2-phenylpropionic acid and the like.

Examples of the carboxylic acid (2) also include, as a cyclopropane compound, for example, cyclopropanecarboxylic acid compound of formula (4) (hereinafter, referred to as cyclopropanecarboxylic acid compound (4)):

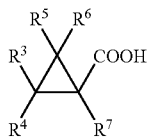

(4)

wherein, $R^3$, $R^4$, $R^5$, $R^6$ and $R^7$ each are independently a hydrogen atom, a halogen atom, an alkyl, alkenyl, alkynyl, aralkyl or aryl group which may be substituted.

In the cyclopropanecarboxylic acid compound (4), with respect to the definitions of the halogen atom, and the alkyl, alkynyl, alkenyl, aryl and aralkyl groups which may be substituted represented by $R^3$ to $R^7$, the definitions of the same groups defined in connection with $R^2$ are referred to.

Examples of the cyclopropanecarboxylic acid compound (4) include, for example, cyclopropanecarboxylic acid, 2-fluorocyclopropanecarboxylic acid, 2,2-dichlorocyclopropanecarboxylic acid, 2,2-dimethyl-3-(dimethoxymethyl)cyclopropanecarboxylic acid, 2,2,3,3-tetramethylcyclopropanecarboxylic acid, 2,2-dimethyl-3-(1-propenyl)cyclopropanecarboxylic acid, 2,2-dimethyl-3-(2-methyl-1-propenyl)cyclopropanecarboxylic acid, 2,2-dimethyl-3-(3-methyl-2-butenyl-)cyclopropanecarboxylic acid, 2,2-dimethyl-3-(2,2-dichlorovinyl)cyclopropanecarboxylic acid, 2,2-dimethyl-3-(2,2,2-trichloroethyl)cyclopropanecarboxylic acid, 2,2-dimethyl-3-(2-chloro-2-fluorovinyl)cyclopropanecarboxylic acid, 2,2-dimethyl-3-(2-bromovinyl)cyclopropanecarboxylic acid, 2,2-dimethyl-3-(2,2-dibromovinyl)cyclopropanecarboxylic acid, 2,2-dimethyl-3-(1,2,2,2-tetrabromoethyl)cyclopropane-carboxylic acid, 2,2-dimethyl-3-(1,2-dibromo-2,2,-dichloroethyl) cyclopropanecarboxylic acid, 2,2-dimethyl-3-(2-chloro-3,3,3-trifluoro-1-propenyl)cyclopropanecarboxylic acid, 2,2-dimethyl-3-{3,3,3-trifluoro-2-(trifluoromethyl)-1-propenyl}cyclopropanecarboxylic acid, 2,2-dimethyl-3-(2-phenyl-1-propenyl)cyclopropanecarboxylic acid, 2,2-dimethyl-3-(2-phenylvinyl)cyclopropanecarboxylic acid, 2,2-dimethyl-3-(2-methyl-3-phenyl-2-butenyl)cyclopropanecarboxylic acid, 2,2-dimethyl-3-{(2,2-difluorocyclopropylidene)methyl}cyclo-propanecarboxylic acid, 2,2-dimethyl-3-{2-(tert-butoxycarbonyl)vinyl}cyclopropanecarboxylic acid, 2,2-dimethyl-3-{2-fluoro-2-(methoxycarbonyl) vinyl}cyclopropanecarboxylic acid, 2,2-dimethyl-3-{2-fluoro-2-(ethoxycarbonyl)vinyl}cyclopropanecarboxylic acid, 2,2-dimethyl-3-{2-fluoro-2-tert-butoxycarbonyl) vinyl}cyclo-propanecarboxylic acid, 2,2-dimethyl-3-[2-{2,2,2-trifluoro-1-(trifluoromethyl)ethoxycarbonyl}-vinyl]cyclopropanecarboxylic acid, 2,2-dimethyl-3-(2-aza-2-methoxyvinyl)cyclopropanecarboxylic acid, 2,2-dimethyl-3-(4-aza-4-methoxy-3-methylbuta-1,3-dienyl) cyclopropanecarboxylic acid, 2,2-dimethyl-3-[2-{(tert-butyl)sulfonyl}-2-(tert-butoxycarbonyl)vinyl] cyclopropanecarboxylic acid, 2,2-dimethyl-3-{2,2,2-tribromo-1-(methylsulfonyloxy)ethyl}-cyclopropanecarboxylic acid, 2,2-dimethyl-3-{2,2-dibromo-2-(hydroxysulfonyl)-1-(methoxy) ethyl}cyclopropanecarboxylic acid, 2,2-dimethyl-3-{2,2,2-tribromo-1-(methylsulfonyloxy)ethyl}-cyclopropanecarboxylic acid, 2-methyl-2-ethyl-3-(1-propenyl)cyclopropanecarboxylic acid, 2,2-diethyl-3-(2,2-dichlorovinyl)cyclopropanecarboxylic acid, 2-methyl-2-phenyl-3-(2-methyl-1-propenyl)cyclopropanecarboxylic acid and the like.

Preferably $R^3$, $R^4$, $R^5$, $R^6$ and $R^7$ are the same or different and independently represent hydrogen, halogen, phenyl, methyl, ethyl, dimethoxymethyl, 1-propenyl, 2-methyl-1-propenyl, 3-methyl-2-butenyl, 2,2-dichlorovinyl, 2,2,2-trichloroethyl, 2-chloro-2-fluorovinyl, 2-bromovinyl, 2,2-dibromovinyl, 1,2,2,2-tetrabromoethyl, 1,2-dibromo-2,2,-dichloroethyl, 2-chloro-3,3,3-trifluoro-1-propenyl, 3,3,3-trifluoro-2-(trifluoromethyl)-1-propenyl, 2-phenyl-1-propenyl, 2-phenylvinyl, 2-methyl-3-phenyl-2-butenyl, 2,2-difluorocyclopropylidene)methyl, 2-(tert-butoxycarbonyl) vinyl, 2-fluoro-2-(methoxycarbonyl)vinyl, 2-fluoro-2-(ethoxycarbonyl)vinyl, 2-fluoro-2-(tert-butoxycarbonyl) vinyl, 2-{2,2,2-trifluoro-1-(trifluoromethyl) ethoxycarbonyl}vinyl, 2-aza-2-methoxyvinyl, 4-aza-4-methoxy-3-methylbuta-1,3-dienyl, 2-{(tert-butyl)sulfonyl}-2-(tert-butoxycarbonyl)vinyl, 2,2,2-tribromo-1-(methylsulfonyloxy)ethyl, or 2,2-dibromo-2-(hydroxysulfinyl)-1-(methoxy)ethyl, and more preferably $R^5$ and $R^6$ represent methyl, and $R^7$ represents hydrogen.

Suitably used cyclopropanecarboxylic acid compound (4) are 2,2-dimethyl-3-(2,2-dichlorovinyl)cyclopropanecarboxylic acid, 2,2-dimethyl-3-(2-methyl-1-propenyl)cyclopropanecarboxylic acid and 2,2-dimethyl-3-(1-propenyl)cyclopropanecarboxylic acid.

The zirconium catalyst can be used in a catalytic amount and it is usually used in an amount of approximately 0.001 to 20 mol % in terms of the zirconium atom contained per mol of the carboxylic acid (2), preferably approximately 0.1 to 10 mol %.

Then amount of the monohydroxy compound (1) that may be used is usually in an excess amount, for example, not less than 1 mol per mol of the carboxylic acid (2). The monohydroxy compound (1) may be used in excess, if necessary, and may be used as solvent.

Alternatively, the monohydroxy compound (1) may be used in an amount of less than 1 mol per mol of the carboxylic acid (2) and after completion of the reaction the unreacted carboxylic acid (2) may be removed or recovered by distillation, and/or extraction.

The reaction step is usually carried out under an atmosphere of inert gas such as argon and nitrogen. The reaction may be, conducted under a normal, pressurized or reduced pressure. The reaction is preferably conducted under normal or reduced pressure. The reaction is preferably conducted by continuously removing by-produced water by distillation.

The reaction may be conducted with or without solvent, and has no limitation in the amount of the solvent. Examples of the solvent that may be used include, for example, a halogenated hydrocarbon solvent such as dichloromethane, chloroform or 1,2-dichloroethane; an aliphatic hydrocarbon solvent such as hexane, heptane, octane or nonane; an aromatic hydrocarbon solvent such as benzene, toluene, xylene or chlorobenzene; an ether solvent such as diethyl ether or tetrahydrofuran. A suitable solvent that makes an azeotropic mixture with water, is used to continuously remove by-produced water.

The reaction is usually conducted in the temperature range of approximately from 20 to 200° C., and preferably, at the temperature, where by-produced water can be removed by distillation or as an azeotropic mixture with the suitable solvent employed.

The reaction is usually conducted by mixing the zirconium catalyst, the monohydroxy compound (1) and the carboxylic acid (2) all at once and heating. Any two components of them, are mixed first and heated and then the other component is added thereto, or any one component of them is heated and thereafter the other two components are added thereto simultaneously.

After completion of the reaction, the zirconium catalyst can be removed from the resulting carboxylic acid ester of formula (3) (hereinafter, referred to as carboxylic acid ester (3)), for example, by washing with water or acidic water. The separated carboxylic acid ester (3) may be further purified by such operations as distillation, recrystallization, and/or column chromatography, if necessary.

Examples of the carboxylic acid ester (3) includes, for example, ethyl acetate, ethyl propionate, ethyl butyrate, ethyl isobutyrate, ethyl valerate, ethyl isovalerate, ethyl pivalate, ethyl hexanoate, ethyl heptanoate, ethyl octanoate, ethyl nonanoate, ethyl decanoate, ethyl laurate, ethyl myristate, ethyl palmitate, ethyl stearate, ethyl acrylate, ethyl propiolate, ethyl methacrylate, ethyl crotonate, ethyl isocrotonate, ethyl fumarate, ethyl maleate, ethyl mesaconate, ethyl citraconate, ethyl cinnamate, ethyl benzoate, ethyl naphthoate, ethyl toluate, ethyl anisate, ethyl piperonylate, ethyl nicotinate, ethyl isonicotinate, phenylethyl acetate and 2-phenylethyl propionate; those that have an alkyl group which may be substituted such as a methyl group and an n-propyl group instead of an ethyl group in ester moiety; and those that have an aralkyl group which may be substituted such as a benzyl group, a 2,3,5,6-tetrafluoro-4-methylbenzyl group and a 2,3, 5,6-tetrafluoro-4-(methoxymethyl)benzyl group instead of an ethyl group in ester moiety.

The process of the invention is suitably used for the production of the cyclopropanecarboxylic acid ester of formula (5) (hereinafter, referred to as cyclopropanecarboxylic acid ester (5)):

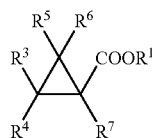

(5)

wherein, $R^3$, $R^4$, $R^5$, $R^6$ and $R^7$ are as defined in connection with formula (4) above, and $R^1$ is as defined in connection with formula (1) or as defined so far as preferable.

Examples of the cyclopropanecarboxylic acid ester (5) include, for example, ethyl cyclopropanecarboxylate, ethyl 2-fluorocyclopropanecarboxylate, ethyl 2,2-dichlorocyclopropanecarboxylate, ethyl 2,2-dimethyl-3-(dimethoxymethyl)cyclopropanecarboxylate, ethyl 2,2,3,3-tetramethylcyclopropanecarboxylate, ethyl 2,2-dimethyl-3-(1-propenyl) cyclopropanecarboxylate, ethyl 2,2-dimethyl-3-(2-methyl-1-propenyl)cyclopropanecarboxylate, ethyl 2,2 dimethyl-3-(3-methyl-2-butenyl)cyclopropanecarboxylate, ethyl 2,2-dimethyl-3-(2,2-dichlorovinyl)cyclopropanecarboxylate, ethyl 2,2-dimethyl-3-(2,2,2-trichloroethyl)cyclopropanecarboxylate, ethyl 2,2-dimethyl-3-(2-chloro-2-fluorovinyl)cyclopropanecarboxylate, ethyl 2,2-dimethyl-3-(2-bromovinyl)cyclopropanecarboxylate, ethyl 2,2-dimethyl-3-(2,2-dibromovinyl)cyclopropanecarboxylate, ethyl 2,2-dimethyl-3-(2,2,2-tetrabromoethyl)cyclopropanecarboxylate, ethyl 2,2-dimethyl-3-(1,2-dibromo-2,2,-dichloroethyl)cyclopropanecarboxylate, ethyl 2,2-dimethyl-3-(2-chloro-3,3,3-trifluoro-1-propenyl)cyclopropanecarboxylate, ethyl 2,2-dimethyl-3-{3,3,3-trifluoro-2-(trifluoromethyl)-1-propenyl}cyclopropanecarboxylate, ethyl 2,2-dimethyl-3-(2-phenyl-1-propenyl)cyclopropanecarboxylate, ethyl 2,2-dimethyl-3-(2-phenylvinyl)cyclopropanecarboxylate, ethyl 2,2-dimethyl-3-(2-methyl-3-phenyl-2-butenyl)cyclopropanecarboxylate, ethyl 2,2-dimethyl-3-{(2,2-difluorocyclopropylidene)methyl}cyclo-propanecarboxylate, ethyl 2,2-dimethyl-3-{2-(tert-butoxycarbonyl)vinyl}cyclopropanecarboxylate, ethyl 2,2-dimethyl-3-{2-fluoro-2-(methoxycarbonyl)vinyl}cyclopropanecarboxylate, ethyl 2,2-dimethyl-3-{2-fluoro-2-(ethoxycarbonyl)vinyl}cyclopropanecarboxylate, ethyl 2,2-dimethyl-3-{2-fluoro-2-(tert-butoxycarbonyl)vinyl}cyclopropanecarboxylate, ethyl 2,2-dimethyl-3-[2-{2,2,2-trifluoro-1-(trifluoromethyl)ethoxycarbonyl}vinyl]cyclopropanecarboxylate, ethyl 2,2-dimethyl-3-(2-aza-2-methoxyvinyl)cyclopropanecarboxylate, ethyl 2,2-dimethyl-3-(4-aza-4-methoxy-3-methylbuta-1,3-dienyl) cyclopropanecarboxylate, ethyl 2,2-dimethyl-3-[2-{(tert-butyl)sulfonyl}-2-(tert-butoxycarbonyl)vinyl] cyclopropanecarboxylate, ethyl 2,2-dimethyl-3-{2,2,2-tribromo-1-(methylsulfonyloxy) ethyl}cyclopropanecarboxylate, ethyl 2,2-dimethyl-3-{2,2-dibromo-2-(hydroxysulfinyl)-1-(methoxy) ethyl}cyclopropanecarboxylate, ethyl 2-methyl-2-ethyl-3-(1-propenyl)cyclopropanecarboxylate, ethyl 2,2-diethyl-3-(2,2-dichlorovinyl)cyclopropanecarboxylate, ethyl 2-methyl-2-phenyl-3-(2-methyl-1-propenyl)-cyclopropanecarboxylate; those that have an alkyl group which may be substituted such as a methyl group or an n-propyl group instead of the ethyl group in the ester moiety; and those that have the aralkyl group which may be substituted such as a benzyl group, a 2,3,5,6-tetrafluoro-4-methylbenzyl group or a 2,3,5,6-tetrafluoro-4-(methoxymethyl)benzyl group instead of the ethyl group in the ester moiety.

The monohydroxy compound (1) and the carboxylic acid (2) may have an asymmetric carbon atom or atoms, and may have not less than two stereoisomers respectively, but any of them may be used in the present invention. According to the present process, the configurations of the alcohol compound and the cyclopropanecarboxylic acid are retained and the corresponding cyclopropanecarboxylic acid ester (5) having the same configurations as their: sources is usually obtained.

EXAMPLE

The following examples illustrate the present invention further in detail, but these do not limit the scope of the present invention. In the following examples, analysis was conducted by using gas chromatography (hereinafter, referred to as GC). Yields were determined by GC internal standard method, and contents of by-products were GC area percentage values without solvent.

Example 1

To 500 ml four-neck flask, 186 g of xylene, 1.70 g of a solution of tetrapropoxyzirconium in propanol (75% in content) and 44.8 g of 2,3,5,6-tetrafluoro-4-(methoxymethyl) benzyl alcohol were charged, and the resultant solution was heated to 143 to 145° C. under stirring at a normal pressure, and then 18.6 g of a mixture of propanol and xylene was distilled off to obtain a solution containing an zirconium catalyst.

The resultant solution was cooled below 80° C., and then 37.0 g of 2,2-dimethyl-3-(2-methyl-1-propenyl)cyclopropanecarboxylic acid, 1.8 g of xylene and 0.74 g of 2,6-di-tert-butyl-4-methylphenol as stabilizing agent were charged.

To the reactor, Dean-Stark trap was equipped, and the reaction was conducted under stirring for eight hours at 145 to 147° C., removing water by-produced during the reaction into the trap, and a solution containing 2,3,5,6-tetrafluoro-4-(methoxymethyl)benzyl 2,2-dimethyl-3-(2-methyl-1-propenyl)cyclopropanecarboxylate was obtained.

Yield: 97% (based on 2,3,5,6-tetrafluoro-4-(methoxymethyl)benzyl alcohol)

Content of by-product: 0.5% of propyl 2,2-dimethyl-3-(2-methyl-1-propenyl)cyclopropanecarboxylate Comparative Example 1

To 500 ml four-neck flask, 186 g of xylene and 1.70 g of absolution of tetrapropoxyzirconium in propanol (75% in content) were charged, and the resultant solution was heated to 143 to 145° C. under stirring at a normal pressure, and then 18.6 g of a mixture of propanol and xylene was distilled off.

The resultant solution was cooled below 80° C., and then 44.8 g of 2,3,5,6-tetrafluoro-4-(methoxymethyl)benzyl alcohol, 37.0 g of 2,2-dimethyl-3-(2-methyl-1-propenyl)cyclopropanecarboxylic acid, 18 g of xylene and 0.74 g of 2,6-di-tert-butyl-4-methylphenol as stabilizing agent were charged.

To the reactor, Dean-Stark trap was equipped, and the reaction was conducted under stirring for eight hours at 145 to 147° C., removing water by-produced during the reaction into the trap, and a solution containing 2,3,5,6-tetrafluoro-4-(methoxymethyl)benzyl 2,2-dimethyl-3-(2-methyl-1-propenyl)cyclopropanecarboxylate was obtained.

Yield: 97% (based on 2,3,5,6-tetrafluoro-4-(methoxymethyl)benzyl alcohol.

Content of by-product: 5.2% of propyl 2,1-dimethyl-3-(2-methyl-1-propenyl)cyclopropanecarboxylate.

Example 2

To 500 ml four-neck flask, 186 g of xylene and 1.70 g of a solution of tetrapropoxyzirconium in propanol (75% in content) were charged. In the resultant solution, 0.42 g of propanol as solvent was contained.

The resultant solution was heated to 143 to 145° C. under stirring at a normal pressure, and 15.9 g of a mixture of propanol and xylene was distilled off. Analysis of the distilled mixture by GC internal standard method showed that 0.38 g of propanol was contained therein.

The resultant solution was cooled below 80° C., and then 44.8 g of 2,3,5,6-tetrafluoro-4-(methoxymethyl)benzyl alcohol, 10 g of xylene and 0.74 g of 2,6-di-tert-butyl-4-methylphenol as stabilizing agent were charged. The mixture was heated to 143 to 145° C. under stirring at a normal pressure, and 68.3 g of a mixture of propanol and xylene was distilled off to obtain a solution containing a zirconium catalyst. Analysis of the distilled mixture by GC internal standard method showed that 0.94 g of propanol was contained therein. A theoretical amount of propanol produced by exchanging all propoxide contained in tetrapropoxyzirconium is 0.92 g. Thus, it is clear that, by this stage of operations, propanol in the solution was almost entirely distilled off, a ligand exchange was progressed quantitatively, and tetra(2,3,5,6-tetrafluoro-4-(methoxymethyl)benzyloxyzirconium was contained as main constituent in the solution.

The resultant solution was cooled below 80° C., and then 37.0 g of 2,2-dimethyl-3-(2-methyl-1-propenyl)cyclopropanecarboxylic acid was charged thereto.

To the reactor, Dean-Stark trap was equipped, and the reaction was conducted with stirring for eight hours at 145 to 147° C., removing water by-produced during the reaction into the trap, and a solution containing 2,3,5,6-tetrafluoro-4-(methoxymethyl)benzyl 2,2-dimethyl-3-(2-methyl-1-propenyl)cyclopropanecarboxylate was obtained.

Yield: 98% (based on 2,3,5,6-tetrafluoro-4-(methoxymethyl)benzyl alcohol.

Content of by-product: propyl 2,2-dimethyl-3-(2-methyl-1-propenyl)cyclopropanecarboxylate was not detected (detection lower limit: 0.04%).

What is claimed is:

1. A process for preparing a carboxylic acid ester of formula (3):

wherein $R^1$ is
an alkyl group which may be substituted,
an alkenyl group which may be substituted,
an alkynyl group which may be substituted,
an aralkyl group which may be substituted, or
a heteroarylalkyl group which may be substituted, and
$R^2$ is
an alkyl group which may be substituted,
an alkenyl group which may be substituted,
an alkynyl group which may be substituted,
an aryl group which may be substituted,
a heteroaryl which may be substituted,
an aralkyl group which may be substituted, or
a heteroarylalkyl group which may be substituted, which process comprises the steps of
reacting a monohydroxy compound of formula (1):

wherein $R^1$ is as defined above, with a zirconium compound of formula (6):

wherein $R^8$ is an alkyl group or an aryl group which may be substituted and is not the same as $R^1$, to prepare a zirconium compound of formula (8):

wherein $R^1$ and $R^8$ have the same meanings as defined above, and n is an integer of 1 to 4, or mixtures thereof, and
reacting a carboxylic acid of formula (2):

wherein $R^2$ is as defined above, with the same monohydroxy compound of formula (1) used above in the presence of the zirconium compound prepared above.

2. A process according to claim 1, wherein the carboxylic acid of formula (2) is a cyclopropanecarboxylic acid compound of formula (4)

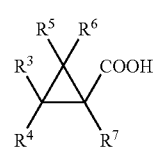

wherein, $R^3$, $R^4$, $R^5$, $R^6$ and $R^7$ each independently represents
a hydrogen atom, a halogen atom,
an alkyl group which may be substituted,
an alkenyl group which may be substituted,
an alkynyl group which may be substituted,
an aralkyl group which may be substituted,
an aryl group which may be substituted, or a heteroaryl group which may be substituted,
and the resultant carboxylic acid ester is a cyclopropanecarboxylic acid ester of formula (5)

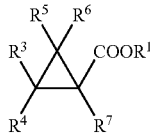

(5)

wherein $R^1$, $R^3$, $R^4$, $R^5$, $R^6$ and $R^7$ are as defined.

3. A process according to claim 2, wherein $R^3$, $R^4$, $R^5$, $R^6$ and $R^7$ are the same or different and independently represent hydrogen, halogen, phenyl, methyl, ethyl, dimethoxymethyl, 1-propenyl, 2-methyl-1-propenyl, 3-methyl-2-butenyl, 2,2-dichlorovinyl, 2,2,2-trichloroethyl, 2-chloro-2-fluorovinyl, 2-bromovinyl, 2,2-dibromovinyl, 1,2,2,2-tetrabromoethyl, 1,2-dibromo-2,2,-dichloroethyl, 2-chloro-3,3,3-trifluoro-1-propenyl, 3,3,3-trifluoro-2-(trifluoromethyl)-1-propenyl, 2-phenyl-1-propenyl, 2-phenylvinyl, 2-methyl-3-phenyl-2-butenyl, 2,2-difluorocyclopropylidene)methyl, 2-(tert-butoxycarbonyl)vinyl, 2-fluoro-2-(methoxycarbonyl)vinyl, 2-fluoro-2-(ethoxycarbonyl)vinyl, 2-fluoro-2-(tert-butoxycarbonyl)vinyl, 2-{2,2,2-trifluoro-1-(trifluoromethyl) ethoxycarbonyl}-vinyl, 2-aza-2-methoxyvinyl, 4-aza-4-methoxy-3-methylbuta-1,3-dienyl, 2-{(tert-butyl)sulfonyl}-2-(tert-butoxycarbonyl)vinyl, 2,2,2-tribromo-1-(methylsulfonyloxy)ethyl, or 2,2-dibromo-2-(hydroxysulfinyl)-1-(methoxy)ethyl.

4. A process according to claim 2, wherein the cyclopropanecarboxylic acid compound of formula (4) is 2,2-dimethyl-3-(2,2-dichlorovinyl)cyclopropanecarboxylic acid, 2,2-dimethyl-3-(2-methyl-1-propenyl)cyclopropanecarboxylic acid, or 2,2-dimethyl-3-(1-propenyl)cyclopropanecarboxylic acid.

5. A process according to claim 1 or 3, wherein the monohydroxy compound of formula (1) is a primary alcohol.

6. A process according to claim 2, wherein the monohydroxy compound of formula (1) is a benzyl group which may be substituted.

7. A process according to claim 2 or 3, wherein $R^1$ represents a $C_{7-20}$ aralkyl group which may be substituted with at least one member selected from the group consisting of
a halogen atom, and
$C_{1-14}$ alkyl, phenyl, phenoxy, $C_{1-4}$ alkoxy and $C_{2-4}$ alkoxyalkyl groups which may be substituted with a halogen atom,
a propargyl group, a cyano group, a nitro group, and a $C_3$ haloacyloxy-methyl group.

8. A process according to claim 7, wherein $R^1$ is a benzyl group which may be substituted with at least one member selected from the group consisting of a halogen atom, a methyl group, a phenyl group, a phenoxy group, a halophenoxy group, a propargyl group, a halomethyl, a halomethoxy group, a cyano group, nitro, a methoxymethyl group and a halogen-substituted methoxymethyl group.

9. A process according to claim 2, 3 or 4, wherein the monohydroxy compound of formula (1) is 4-(2-thienyl)indan-2-ol, (2,3,6-trifluoro-4-pyridyl)methane-1-ol, (1-prop-2-ynyl-2-methylindole-3-yl)methane-1-ol, {1-prop-2-ynyl-2-(trifluoromethyl)indole-3-yl}methane-1-ol, 2-furylmethyl alcohol, 3-furylmethyl alcohol, (5-phenoxy-3-furyl)methyl alcohol, (5-benzyl-3-furyl)methane-1-ol, {5-(difluoromethyl)-3-furyl}methane-1-ol, 5-propargylfurfuryl alcohol, (5-methylisoxazol-3-yl)methane-1-ol, 1-{2-(trifluoromethyl)-1,3-thiazol-4-yl}prop-2-yne-1-ol, 1-{2-(trifluoromethoxy)-1,3-thiazol-4-yl}prop-2-yne-1-ol, 1-{1-prop-2-ynyl-5-(trifluoromethyl)pyrrole-3-yl}prop-2-yne-1-ol, (1-prop-2-ynylpyrrole-3-yl)methane-1-ol, 3-(hydroxymethyl)-1-propynyl-imidazolidin-2,4-dione, 2-(hydroxymethyl)-4,5,6,7-tetrahydroisoindole-1,3-dione, {1-(2-propynyl)pyrrole-3-yl}methane-1-ol, 5-(hydroxymethyl)-4-methyl-(2-propynyl)-1,3-thazolin-2-one, {1-(2-propynyl)-5-(trifluoromethyl)-4-pyrazolyl}methane-1-ol, 1-{1-(2-propynyl)-5-(trifluoromethyl)pyrrole-3-yl}prop-2-yne-1-ol, 1-{2-(trifluoromethyl)-1,3-thiazol-4-yl}prop-2-yne-1-ol, or 1-{2-(trifluoromethoxy)-1,3-thiazol-4-yl}prop-2-yne-1-ol.

10. A process according to claim 6, wherein the monohydroxy compound of formula (1) is a benzyl alcohol substituted with a halogen atom.

11. A process according to claim 1, wherein the zirconium compound of formula (6) is any one selected from the group consisting of tetramethoxyzirconium, tetraethoxyzirconium, tetrapropoxyzirconium and tetrabutoxyzirconium.

12. A process according to claim 11, wherein the reaction of the monohydroxy compound of formula (1) with the carboxylic acid of formula (2) is conducted after removing a hydroxy compound of formula (7):

$$R^8OH \quad (7)$$

wherein $R^8$ has the same meanings as above, which is by-produced by reacting the zirconium compound of formula (6) with the monohydroxy compound of formula (1).

13. A process according to claim 12, wherein the hydroxy compound of formula (7) is removed in the presence of a solvent.

14. A process according to claim 13, wherein the solvent is a solvent having higher boiling point than that of the hydroxy compound of formula (7), a solvent which can make an azeotrope with the hydroxy compound of formula (7), or a mixture of the solvent.

* * * * *